US00PP17086P2

(12) United States Plant Patent
Bradford

(10) Patent No.: US PP17,086 P2
(45) Date of Patent: Sep. 5, 2006

(54) NECTARINE TREE NAMED 'RED BRIGHT'

(50) Latin Name: *Prunus persica*
Varietal Denomination: RED BRIGHT

(76) Inventor: Lowell Glen Bradford, 10237 E. Mariposa Way, Le Grand, CA (US) 95333

( * ) Notice: Subject to any disclaimer, the term of this patent is extended or adjusted under 35 U.S.C. 154(b) by 0 days.

(21) Appl. No.: 11/311,176

(22) Filed: Dec. 20, 2005

(51) Int. Cl.
*A01H 5/00* (2006.01)

(52) U.S. Cl. ..... Plt./190
(58) Field of Classification Search ..... Plt./190
See application file for complete search history.

(56) References Cited
U.S. PATENT DOCUMENTS

PP7,918 P 7/1992 Bradford

*Primary Examiner*—Kent Bell
*Assistant Examiner*—Annette H Para

(57) ABSTRACT

The present invention relates to a nectarine tree, *Prunus persica,* and more particularly to a new and distinct variety broadly characterized by a medium size, vigorous, hardy, self-fertile, productive and regular bearing tree. The fruit matures under the ecological conditions described in late June, with first picking on Jun. 24, 2005. The fruit is uniformly large in size, mildly acidic and sweet in flavor, globose in shape, clingstone in type, firm in texture, yellow in flesh color, and full dark red in skin color. The variety was developed as a first generation cross using 'Ruby Diamond' (U.S Plant Pat. No. 7,918) yellow flesh nectarine as the selected seed parent and an unnamed yellow flesh peach (unpatented) as the selected pollen parent.

1 Drawing Sheet

Botanical classification: *Prunus persica.*
Variety denomination: 'RED BRIGHT'.

BACKGROUND OF THE VARIETY

In a continuing effort to improve the quality of shipping fruits, I, the inventor, typically hybridize a large number of peach, nectarine, plum, apricot, and cherry seedlings each year. The present invention relates to a new and distinct variety of nectarine tree, which has been denominated varietally as 'RED BRIGHT'. The present variety was hybridized by me in 1996, grown as a seedling on its own root in my greenhouse, and transplanted to a cultivated area of my experimental orchard at Bradford Farms near Le Grand, Calif., in Merced County (San Joaquin Valley).

The variety was developed as a first generation cross using 'Ruby Diamond' (U.S. Plant Pat. No. 7,918) yellow flesh nectarine as the selected seed parent and an unnamed yellow flesh peach (unpatented) as the selected pollen parent. A single tree from the stated cross was selected as the claimed variety. Subsequent to origination of the present variety of nectarine tree, I asexually reproduced it by budding and grafting in the experimental orchard described above, and such reproduction of plant and fruit characteristics were true to the original plant in all respects. The reproduction of the variety included the use of 'Nemaguard' (unpatented) rootstock upon which the present variety was compatible and true to type.

The present variety is most similar to its selected seed parent, 'Ruby Diamond' (U.S. Plant Pat. No. 7,918) nectarine, by producing nectarines that are nearly globose in shape, very firm in texture, yellow in flesh color, and full red in skin color, but is distinguished therefrom by requiring less chilling hours and by producing fruit that is larger in size, clingstone instead of freestone in type, and that matures about seven days earlier.

SUMMARY OF VARIETY

In summary, the present variety is characterized by a medium size, vigorous, hardy, self-fertile, productive and regular bearing tree. The fruit matures under the ecological conditions described in late June, with first picking on Jun. 24, 2005. The fruit is uniformly large in size, mildly acidic and sweet in flavor, globose in shape, clingstone in type, firm in texture, yellow in flesh color, and full dark red in skin color.

DRAWING

The accompanying photograph consists of four whole fruits positioned to display the characteristics of the skin color and form, one fruit divided transversely to the suture plane to reveal the flesh and stone, a lower inset to reveal blossoms in various stages, two full size leaves, and a typical tip shoot.

POMOLOGICAL CHARACTERISTICS

Referring now more specifically to the pomological characteristics of this new and distinct variety of nectarine tree, the following has been observed under the ecological conditions prevailing near Le Grand, Merced County (San Joaquin Valley), Calif., and was developed at the state of firm ripe on Jun. 28, 2005, on the original tree during its ninth growing season. All major color code designations are by reference to the Inter-Society Color Council, National Bureau of Standards. Common color names are also used occasionally.

Tree

Size: Medium, reaching a height of 10' [3.05 m.] and a spread of 10' [3.05 m.] after nine growing seasons utilizing typical dormant pruning.

Vigor: Vigorous, responding typically to irrigation and fertilization. The variety grows about 3' [0.91 m.] of surplus top-growth during the spring and summer. The plant should be grown on a standard commercial rootstock for production purposes.

Growth: Upright and dense.

Form: Vase formed.

Hardiness: Hardy with respect to central California winters.

Heat tolerance: Observed to perform adequately in typical central California climatic conditions, which typically include extended periods of heat.

Drought tolerance: Variety is developed for commercial orchards and requires regular irrigation.

Production: Very productive, thinning necessary.

Fertility: Self-fertile.

Bearing: Regular bearer with no alternate bearing yet observed.

Approximate chilling requirement: 650 hours.

Trunk:

*Size.*—Medium, with a maximum diameter of 5⅜" [137 mm.] after the ninth growing season.

*Texture.*—Shaggy.

*Bark color.*—Dark yellowish brown [78. d.yBr].

*Lenticels.*—Approximate Number Per Square Inch: 12. Color: Brilliant orange yellow [67. brill.OY]. Typical Size: 3/16" [4.8 mm.] to 7/16" [11.1 mm.]. Shape: Eye-shaped to elongated.

Branches:

*Size.*—Diameter of limb is 2¾" [69.9 mm.] measured 12" above the crotch, 1¾" [44.5 mm.] measured 12" above first fork.

*Texture.*—Smooth on first year wood, increasing roughness with age.

*Color.*—1st Year Wood Topside: Grayish red [19. gy.R]. 1st Year Wood Underside: Brilliant yellow green [116. brill.YG]. Older Wood: Deep yellowish brown [75. deep yBr].

*Lenticels.*—Average Number Per Square Inch: 40. Color: Light orange yellow [70. l.OY]. Typical size: 1/16" [1.6 mm.] to ⅛" [3.2 mm.]. Shape: Eye-shaped to elongated.

Leaves:

*Size.*—Medium. Average Length: 5½" [140 mm.]. Average Width: 1⅜" [35 mm.].

*Arrangement.*—Alternate.

*Thickness.*—Medium.

*Form.*—Elliptical.

*Apex.*—Acuminate.

*Base.*—Acute, with a base angle of 65 to 85 degrees.

*Surface.*—Smooth.

*Color.*—Dorsal Surface: Moderate olive green [125. m.OlG]. Ventral Surface: Moderate yellowish green [136. m.yG].

*Margin.*—Finely serrate.

*Venation.*—Pinnately net veined.

*Vein color.*—Light yellow green [119. l.YG].

*Petiole.*—Average Length: ⅜" [9.5 mm.]. Average Thickness: 1/16" [1.6 mm.]. Color: Brilliant yellow green [116. brill.YG].

*Stipules.*—Number: 2 to 6 per growing tip. Average length: ⅜" [9.5 mm.]. Color: Very yellow green [115. v.YG] becoming Dark grayish reddish brown [47. d.gy.rBr] with maturity.

*Glands.*—Number: 2 to 6. Position: Mostly opposite, some alternate. Size: Medium. Form: Reniform. Color: Brilliant yellow green [116. brill.YG] becoming Moderate reddish brown [43. m.rBr] with age.

*Leaf buds.*—Pointed, Moderate in size.

Flower buds:

*Hardiness.*—Hardy, with respect to central California winters.

*Diameter.*—Typically 5/16" [7.9 mm.] 1 week before bloom.

*Length.*—Typically ½" [12.7 mm.] 1 week before bloom.

*Form.*—Not appressed.

*Surface.*—Pubescent.

*Color.*—Moderate purplish pink [250. m.pPk].

Flowers: Perfect, complete, perigynous, usually a single pistil, typically thirty or more stamens, five sepals and petal locations alternately positioned.

*Type.*—Showy, large.

*Average flower diameter.*—1¾" [44.5 mm.].

*Number of petals.*—Usually five, with a very small percentage of double blossoms.

*Petal shape.*—Circular to oval.

*Petal margin.*—Somewhat wavy.

*Average petal diameter.*—11/16" [17.5 mm.].

*Average petal length.*—¾" [19.1 mm.].

*Petal apex.*—Rounded.

*Petal base.*—Rounded to somewhat truncate.

*Petal color.*—Pale pink [7. p.Pk] toward the apex, Moderate purplish pink [250. m.pPk] toward the base.

*Anther color.*—Strong reddish orange [35. s.rO] over Light yellow [86. l.Y] centers at bloom onset.

*Stigma color.*—Light greenish yellow [101. l.gY].

*Sepal color.*—Dark purplish red [259. d.pR].

*Sepal length.*—¼" [6 mm.].

*Sepal width.*—3/16" [5 mm.].

*Average pistil length.*—11/16" [17.5 mm.].

*Average stamen length.*—⅝" [15.9 mm.].

*Fragrance.*—Moderate.

*Blooming period.*—Medium to late compared with other varieties.

*Onset of bloom.*—One percent on Feb. 22, 2005.

*Date of full bloom.*—Mar. 2, 2005.

*Duration of bloom.*—One to two weeks, dependent on ambient temperature.

*Number per cluster.*—1 to 3 with single flowers most common.

FRUIT

Maturity when described: Firm ripe, Jun. 28, 2005.

Date of first picking: Jun. 24, 2005.

Date of last picking: Jul. 8, 2005.

Size: Uniform, large.

*Average diameter axially.*—3" [76.2 mm.].

*Average diameter across suture plane.*—2⅞" [73.0 mm.].

*Typical weight.*—8.2 ounces [232 grams].

Form: Globose.

*Longitudinal section form.*—Round to slightly oval.

*Axial view.*—Round.

Suture: A shallow groove extending from the base, along the side, and beyond the apex, with increasing sharpness and slight depressions near the pistil point.

Ventral surface: Rounded, lipped throughout, slightly stronger on one side.

Lips: Slightly unequal.

Cavity: Flaring, elongated in the suture plane, suture showing on one side, Very yellow [82. v.Y] stem markings typical.

*Depth.*—⅝" [15.9 mm.].

*Breadth.*—1" [25.4 mm.].

Base: Truncate, but somewhat cordate if viewed parallel to the suture.

Apex: Rounded, but somewhat cordate if viewed parallel to the suture.
Pistil point: Apical, negligible in length, depressed within the suture.
Stem: Medium.
*Average length.*—⅜" [9.5 mm.].
*Average width.*—3/16" [4.8 mm.].
Skin:
*Thickness.*—Medium.
*Surface.*—Smooth.
*Tenacity.*—Tenacious to flesh.
*Astringency.*—Nonastringent.
*Tendency to crack.*—None observed.
*Color.*—Very deep red [14. v.deep R] over a Moderate red [15. m.R.] background with very slight Light orange yellow [70. l.OY] freckling toward the apex.
Flesh:
*Color.*—Brilliant Yellow [83. brill.Y] with Dark red [16. d.R.] flecking toward the skin and very near the stone.
*Surface of pit cavity.*—Moderate red [15 m.R] and Brilliant Yellow [83. brill.Y] broken fibers when twisted from stone.
*Amygdalin.*—Abundant.
*Juice.*—Abundant, rich.
*Texture.*—Firm, crisp.
*Fibers.*—Abundant, fine.
*Ripens.*—Earlier at the apex.
*Flavor.*—Acid, mild and sweet, typically 12.5 brix.
*Aroma.*—Slight.
*Eating quality.*—Very good.

STONE

Type: Clingstone.
Form: Oval.
Hilum: Narrow.
Base: Straight.
Apex: Acute, with an average tip angle of 80 degrees and a length of ⅛" [3.2 mm.].
Sides: Equal.
Surface: Irregularly furrowed toward the apex, and pitted toward the base.
Ridges: Jagged toward the base.
External color: Dark yellowish brown [78. d.yBr].
Pit wall color when cracked: Light orange yellow [70. l.OY].
Cavity surface color: Light yellowish brown [76. l.yBr].
Average pit wall thickness: ¼" [6.4 mm.].
Average width: 1 1/16" [27.0 mm.].
Average length: 1 3/16" [30.2 mm.].
Average breadth: ¾" [19.1 mm.].
Tendency to split: None observed.
Kernel:
*Form.*—Oval.
*Skin color.*—Light yellow [86. l.Y] when first removed.
*Pellicle color.*—Light grayish brown [60. l.gy.Br].
*Vein color.*—Light grayish brown [60. l.gy.Br].
*Taste.*—Sweet.
*Viable.*—Yes.
*Average width.*—½" [12.7 mm.].
*Average length.*—¾" [19.1 mm.].
*Amygdalin.*—Scant.

USE

Market: Fresh market and long distance shipping.
Keeping quality: Good. Fruit quality observed to remain in good condition after 21 days in standard cold room at 36° Fahrenheit [2° Celsius].
Shipping quality: Good.
Resistance to insects: No unusual susceptibilities noted.
Resistance to diseases: No unusual susceptibilities noted.

Other Notes

Although the new variety of nectarine tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of nectarine tree, substantially as illustrated and described, that is most similar to its selected seed parent, 'Ruby Diamond' (U.S. Plant Pat. No. 7,918) nectarine, by producing nectarines that are nearly globose in shape, very firm in texture, yellow in flesh color, and full red in skin color, but is distinguished therefrom by requiring less chilling hours and by producing fruit that is larger in size, clingstone instead of freestone in type, and that matures about seven days earlier.

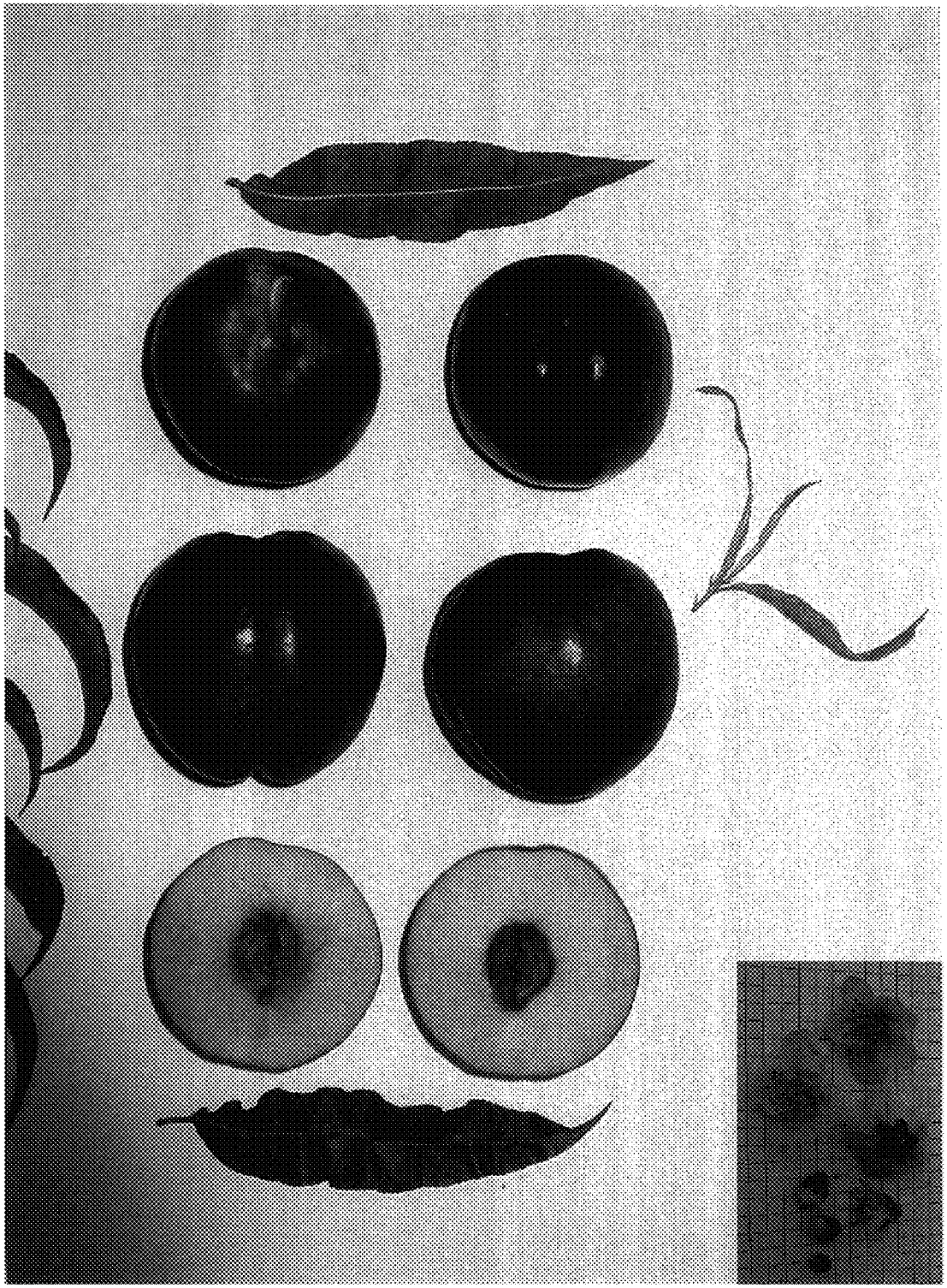

* * * * *